(12) United States Patent
Redda et al.

(10) Patent No.: US 8,546,426 B2
(45) Date of Patent: Oct. 1, 2013

(54) N-AMINOTETRAHYDROISOQUINOLINES AS ANTI-CANCER AGENTS

(75) Inventors: Kinfe Ken Redda, Tallahassee, FL (US); Madhavi Gangapuram, Tallahassee, FL (US)

(73) Assignee: Florida A&M University Board of Trustees, Tallahassee, FL (US)

( * ) Notice: Subject to any disclaimer, the term of this patent is extended or adjusted under 35 U.S.C. 154(b) by 6 days.

(21) Appl. No.: 13/307,701

(22) Filed: Nov. 30, 2011

(65) Prior Publication Data

US 2013/0109716 A1    May 2, 2013

Related U.S. Application Data

(60) Provisional application No. 61/553,338, filed on Oct. 31, 2011.

(51) Int. Cl.
*A61K 31/472*    (2006.01)
*C07D 217/08*    (2006.01)

(52) U.S. Cl.
USPC .......................................... 514/310; 546/143

(58) Field of Classification Search
None
See application file for complete search history.

(56) References Cited

FOREIGN PATENT DOCUMENTS

WO    WO 0162737 A2 * 8/2001

OTHER PUBLICATIONS

Hoeft et al, Angewandte Chemie (1961), vol. 73, No. 24, p. 807.*
Powell et al, Journal of Heterocyclic Chemistry (1983), 20(1), pp. 121-8.*

* cited by examiner

*Primary Examiner* — Zinna Northington Davis
(74) *Attorney, Agent, or Firm* — Thomas Horstemeyer, LLP

(57) ABSTRACT

The compounds herein disclosed are tetrahydroisoquinoline analogs that have modifications on the phenyl rings by introducing groups with various electronic properties. These derivatives of tetrahydroisoquinoline have been shown to have anti-proliferative activity against cells. In particular, the compounds have been found to be effective in inhibiting the proliferation of cancer cells, such as cancer cells that originated in breast tissue. Additionally, it has been shown that the novel compounds have $IC_{50}$ values against the breast cancer cells that are 6-10-fold less than the $IC_{50}$ of tamoxifen.

19 Claims, 4 Drawing Sheets

N-AMINOTETRAHYDROISOQUINOLINES AS ANTI-CANCER AGENTS

CROSS-REFERENCE TO RELATED APPLICATIONS

This application claims priority to U.S. Provisional Patent Application Ser. No. 61/553,338, entitled "N-AMINOTETRAHYDROISOQUINOLINES AS ANTI-CANCER AGENTS" filed on Oct. 31, 2011, the entirety of which is hereby incorporated by reference.

STATEMENT REGARDING FEDERALLY SPONSORED RESEARCH OR DEVELOPMENT

This invention was made with government support under Grant No. G12 RR03020 of the National institutes of Health, National Center of Research Resources, Research Center in Minority Institutions Program of the United States government. The government has certain rights in the invention

TECHNICAL FIELD

The present disclosure is generally related to N-aminotetrahydroisoquinoline compounds and their use in modulating the proliferation of transformed (cancer) cells.

BACKGROUND

Cancer is a disease in which cells in the body grow out of control. Cancer and cancer cells are typically named according to the tissue in which the cells start in the breast, it is called breast cancer. Breast cancer is the second leading cause of cancer-related deaths in women today and is the most common cancer among women, excluding non-melanoma skin cancers. In 2009, an estimated 192,370 new cases of invasive breast cancer were diagnosed among women, as well as an estimated 62,280 additional cases of in situ breast cancer. In 2009, approximately 40,170 women were expected to die from breast cancer.

The nuclear receptor, estrogen receptor (ER) and progesterone receptor (PR) and their associated steroid hormones, are known to play essential roles in the growth of breast tumors, and their status is also employed as diagnostic indicators for endocrine responsiveness and tumor recurrence. The estrogen receptors (ERs) are attractive targets in the treatment of breast cancer and the development of receptor-based breast cancer imaging agents for diagnostic use in biomedical imaging technique positron emission tomography (PET).

Ecteinascidin-743 (ET-743) is a marine tetrahydroisoquinoline alkaloid isolated from the tunicate *Ekteinascidia turbinata* with a potent cytotoxic activity against a variety of tumor cell lines in vitro and against several rodent tumors and human tumor xenografts in vivo. Tetrahydroisoquinoline natural products have been shown to exhibit biological activity, rendering them potential pharmaceutical agents. The tetraydroisoquinoline family of alkaloids includes potent cytotoxic agents that display a range of biological properties such as antitumor and antimicrobial activities studied thoroughly over the past 25 years starting with the isolation of naphthyndinomycin in 1974. 1-Methyl-1,2,3,4-tetrahydraisoquinoline (1-MeTIQ) is considered to be a possible endogenous parkinsonism-preventing agent that is present in the mouse, rat, monkey and human.

SUMMARY

Briefly described, this disclosure provides, among others, embodiments of a compound having the structure:

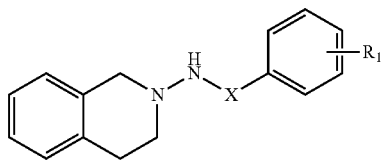

where X is carbonyl or $SO_2$; and $R_1$ can be H, a straight-chain alkyl group, a branched-chain alkyl group, a substituted alkyl group, an alkoxy group, or a halogen; or a salt thereof.

In some embodiments of this aspect of the disclosure, $R_1$ can be $CH_3$, $—OCH_3$, or $—OC_2H_5$.

In some embodiments of this aspect of the disclosure, the halogen can be Cl.

In embodiments of this aspect of the disclosure, can be selected from the group consisting of:

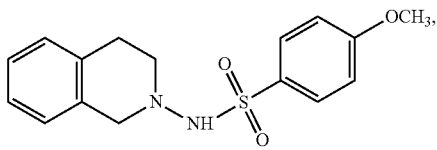

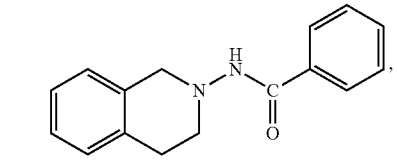

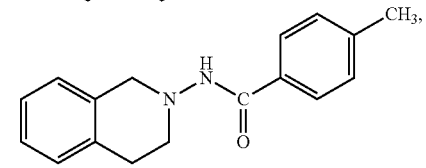

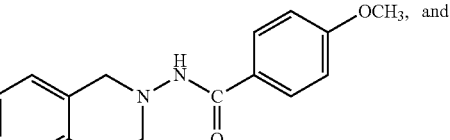

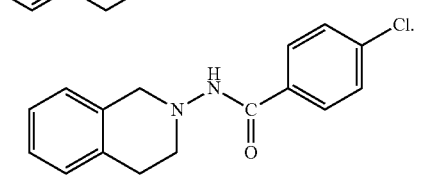

Another aspect of the disclosure encompasses embodiments of a pharmaceutically acceptable composition comprising a compound having the structure:

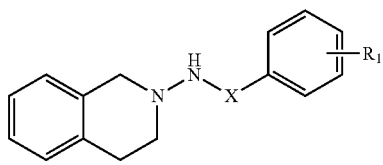

where X is carbonyl or $SO_2$; and $R_1$ can be H, a straight-chain alkyl group, a branched-chain alkyl group, a substituted alkyl group, an alkoxy group, or a halogen;
or a salt thereof, and a pharmaceutically acceptable carrier.

In some embodiments of this aspect of the disclosure, $R_1$ can be H, $CH_3$, —$OCH_3$, or —$OC_2H_5$.

In some embodiments of this aspect of the disclosure, the halogen can be Cl.

In embodiments of this aspect of the disclosure, the compound can be selected from the group consisting of:

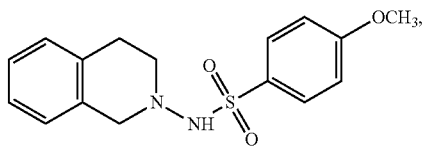

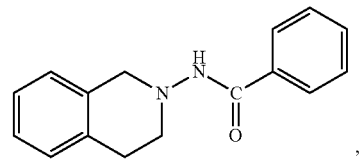

,

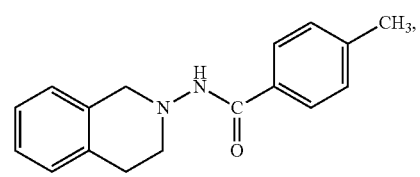

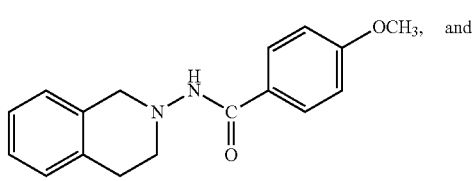 and

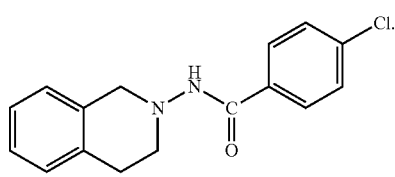

In embodiments of this aspect of the disclosure, the pharmaceutically acceptable composition can be formulated to provide an amount of the compound effective in inhibiting the proliferation of a cell cultured in vitro.

In embodiments of this aspect of the disclosure, the cell can be a cancer cell.

In some embodiments of this aspect of the disclosure, the cell can be a breast cancer cell.

In embodiments of this aspect of the disclosure, the pharmaceutically acceptable composition can be formulated to provide a therapeutically effective amount of the compound for inhibiting the proliferation of a cell in vivo.

In embodiments of this aspect of the disclosure, the in vivo cell can be a cancer cell.

In embodiments of this aspect of the disclosure, the cell can be a breast cancer cell.

Another aspect of the disclosure encompasses embodiments of a method of inhibiting the proliferation of a cell comprising contacting a cell with an effective amount of a compound having the structure:

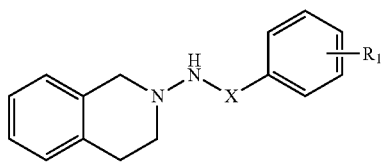

where X is carbonyl or $SO_2$; and $R_1$ can be H, a straight-chain alkyl group, a branched-chain alkyl group, a substituted alkyl group, an alkoxy group, or a halogen;

or a salt thereof, and a pharmaceutically acceptable carrier, thereby reducing the proliferation rate of the cell compared to the proliferation rate of a cell not in contact with the compound.

In some embodiments of this aspect of the disclosure, $R_1$ can be $CH_3$, —$OCH_3$, or —$OC_2H_5$.

In embodiments of this aspect of the disclosure, the compound can be selected from the group consisting of:

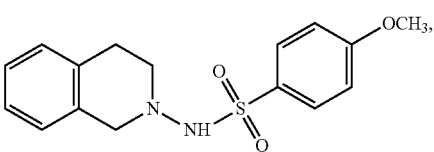

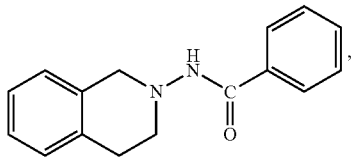

,

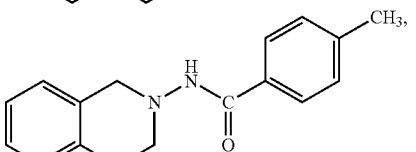

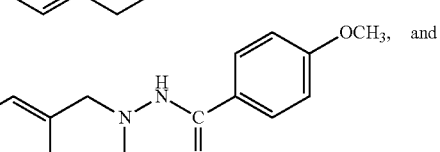 and

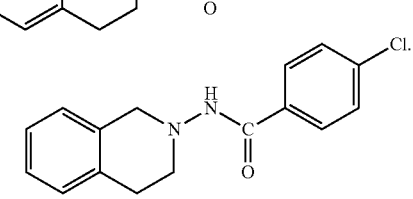

In embodiments of this aspect of the disclosure, the cell can be a cancer cell.

In embodiments of this aspect of the disclosure, the cell can be a breast cancer cell.

In embodiments of this aspect of the disclosure, the cell can be a cultured cell or a cell of an animal or human subject.

BRIEF DESCRIPTION OF THE DRAWINGS

Further aspects of the present disclosure will be more readily appreciated upon review of the detailed description of its various embodiments, described below, when taken in conjunction with the accompanying drawings.

Figure 1:
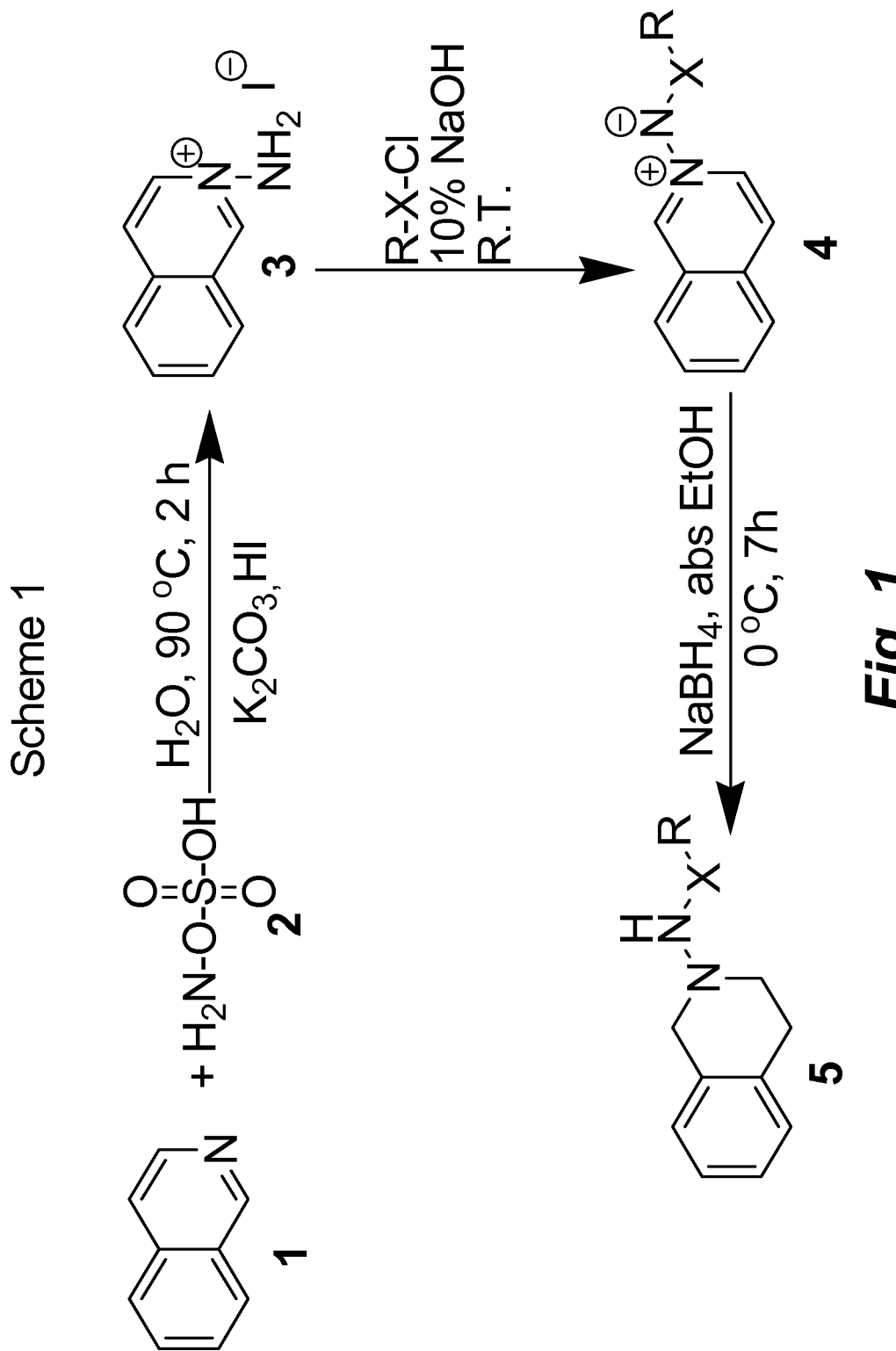
FIG. 1 schematically illustrates the synthesis of substituted N-(3,4-dihydroisoquinolin-2-(1H)-yl)benzamide/benzenesulfonamides.
Figure 2:
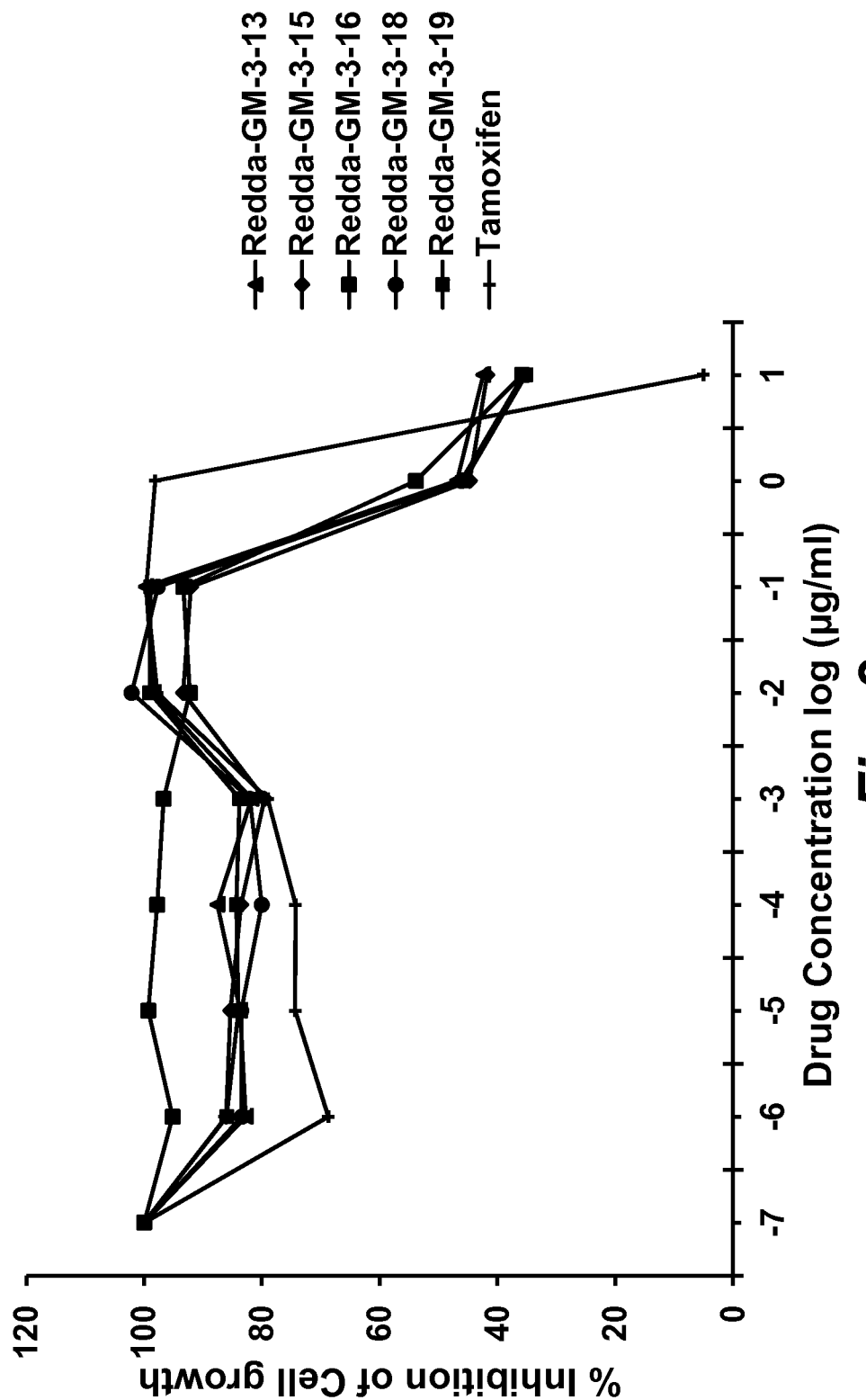
FIG. 2 is a graph illustrating the inhibition of the growth of MCF-7 cells by exposure to the compounds of the disclosure and to tamoxifen.
Figure 3:
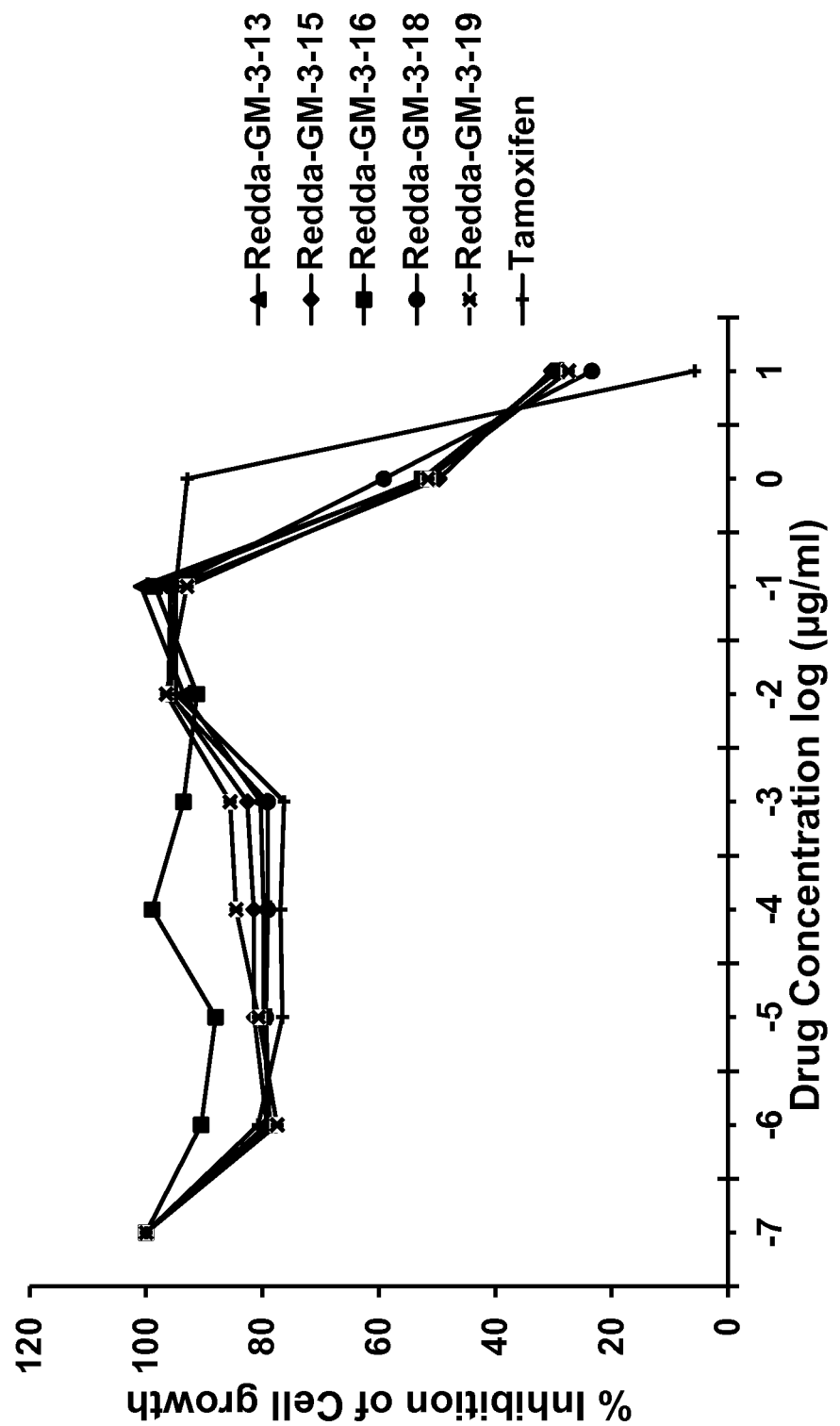
FIG. 3 is a graph illustrating the inhibition of the growth of MDA-MB-231 cells by exposure to the compounds of the disclosure and to tamoxifen.
Figure 4:
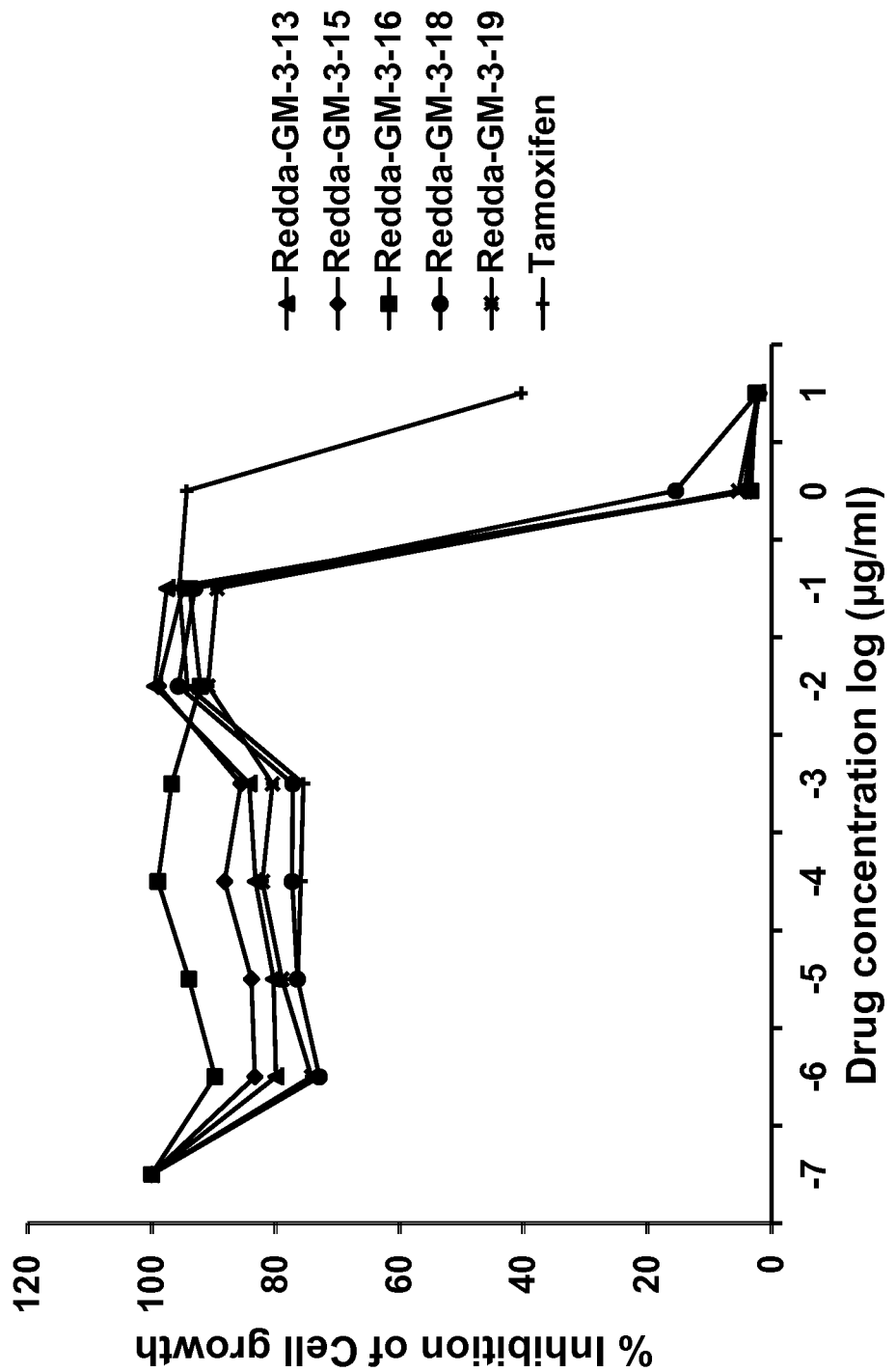
FIG. 4 is a graph illustrating the inhibition of the growth of Ishikawa cells by exposure to the compounds of the disclosure and to tamoxifen.

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and embodiments. It is intended that all such additional systems, methods, features, and advantages be included within this description, be within the scope of the present disclosure.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended embodiments, the singular forms "a," "an," and "the" include plural referents unless the context clearly dictates otherwise. Thus, for example, reference to "a support" includes a plurality of supports. In this specification and in the embodiments that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

DEFINITIONS

The term "sulfonyl", whether used alone or linked to other terms such as alkylsulfonyl or arylsulfonyl, denotes respectively divalent radicals —$SO_2$—.

The terms "sulfamyl," "aminosulfonyl" and "sulfonamidyl," whether alone or used with terms such as "N-alkylaminosulfonyl", "N-arylaminosulfonyl", "N,N-dialkylaminosulfonyl" and "N-alkyl-N-arylaminosulfonyl", denotes a sulfonyl radical substituted with an amine radical, forming a sulfonamide (—$SO_2NH_2$).

The term "carbonyl", whether used alone or with other terms, such as "aminocarbonyl", denotes —(C=O)—.

The term "substituted acid chloride" as used herein refers to compounds having the general formula of R—(C=O)—Cl, wherein R—(C=O) denotes a substituted carbonyl such as, but not limited to, an alkylcarbonyl, an arylcarbonyl, a heterocyclylcarbonyl, an aminocarbonyl, an N-alkylaminocarbonyl, an N,N-dialkylaminocarbonyl, an N-arylaminocarbonyl, and the like.

The terms "alkylcarbonyl" denotes carbonyl radicals which have been substituted with an alkyl radical. Advantageous are "lower alkylcarbonyl" having lower alkyl radicals as described above attached to a carbonyl radical.

The terms "arylcarbonyl" denotes carbonyl radicals substituted with an aryl radical. Advantageous are "optionally substituted phenylcarbonyl" radicals.

The terms "heterocyclylcarbonyl" denotes carbonyl radicals substituted with an heterocyclyl radical. More preferred are "optionally substituted 5-6 membered heterocyclylcarbonyl" radicals.

The term "aminocarbonyl" when used by itself or with other terms such as "aminocarbonylalkyl", "N-alkylaminocarbonyl", "N-arylaminocarbonyl", "N,N-dialkylaminocarbonyl", "N-alkyl-N-arylaminocarbonyl", "N-alkyl-N-hydroxyaminocarbonyl" and "N-alkyl-N-hydroxyaminocarbonylalkyl", denotes an amide group of the formula $H_2NC=O—$.

The terms "N-alkylaminocarbonyl" and "N,N-dialkylaminocarbonyl" denote aminocarbonyl radicals which have been substituted with one alkyl radical and independently with two alkyl radicals, respectively. Advantageous are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The term "aminoalkyl" embraces linear or branched alkyl radicals having one to about ten carbon atoms any one of which may be substituted with one or more amino radicals. Advantageous aminoalkyl radicals are "lower aminoalkyl" radicals having one to six carbon atoms and one or more amino radicals. Examples of such radicals include aminomethyl, aminoethyl, aminopropyl, aminobutyl, and aminohexyl.

The term "cancer", as used herein shall be given its ordinary meaning and is a general term for diseases in which abnormal cells divide without control. Cancer cells can invade nearby tissues and can spread through the bloodstream and lymphatic system to other parts of the body. There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system.

The term "composition" as used herein encompasses a product comprising the specified ingredients in the specified amounts, as well as any product that results, directly or indirectly, from combinations of the specified ingredients in the specified amounts.

"Pharmaceutically acceptable salts" include, but are not limited to, the acid addition salts of compounds of the present disclosure that are formed with inorganic acids (e.g., hydrochloric acid or phosphoric acids) and organic acids (e.g., acetic, oxalic, tartaric, or maleic acid). Salts formed with the free carboxyl groups may also be derived from inorganic bases (e.g., sodium, potassium, ammonium, calcium, or ferric hydroxides), and organic bases (e.g., isopropylamine, trimethylamine, 2-ethylamino-ethanol, histidine, and procaine).

The term "excipient" as used herein refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The terms "effective amount" and therapeutically-effective amount" as used herein means that amount of a compound, material, or composition comprising a compound or composition of the present disclosure, and which is effective for producing a desired therapeutic effect, biological or medicinal response in a tissue system, animal or human that is being sought by a researcher, veterinarian, medical doctor or other clinician, which includes alleviation of the symptoms of the disease or disorder being treated.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or an encapsulating material such as liposomes, polyethylene glycol (PEG), PEGylated liposomes, nanoparticles and the like, involved in carrying or transporting the subject compositions or therapeutic agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "subject" and "subject animal or human" as used herein refers to any animal, including a human, to which a composition according to the disclosure may be delivered or administered.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

Discussion

The present disclosure encompasses embodiments of derivatives of tetrahydroisoquinoline that have anti-proliferative activity against cells. In particular, although not intending to be limiting, the compounds of the disclosure have been found to be effective in inhibiting the proliferation of cancer cells, such as cancer cells that originated in breast tissue. Accordingly, it is contemplated that the compounds of the disclosure may be formulated into pharmaceutically effective compositions for delivery of the anti-proliferative compound to a cultured or in vivo cell, thereby reducing the proliferation of the cell or population of cells compared to the proliferation rate of the cells not exposed to the compound.

The compounds herein disclosed are analogs that maintain the integrity of the tetrahydroisoquinoline moiety, and have modifications on the phenyl rings by introducing groups with various electronic properties. The compounds were synthesized and characterized using NMR, IR and elemental analysis.

As schematically shown in FIG. 1, the starting compound 2-aminoisoquinolinium iodide (3) can be obtained by the reaction of isoquinoline and hydroxylamine-O-sulfonic acid and water, with refluxing at 90° C. for about 2 hrs. Reaction of (3) with substituted acid chlorides or sulfonyl chlorides (4) in 10% KOH solution at room temperature gave stable ylides (5). Sodium borohydride reduction of (5) in absolute ethanol furnished the target compounds. It is contemplated that the reaction schema as shown in FIG. 1 may incorporate the use of any substituted acid chloride or sulfonyl chloride, including, but not limited to, methanesulfonyl chloride, trifluoromethanesulfonyl chloride, ethanesulfonyl chloride, benzenesulfonyl chloride, p-toluenesulfonyl chloride, p-nitrobenzoyl chloride, benzoyl chloride, and the like.

The derivatives were examined for their cytotoxic effects on MCF-7 estrogen receptor-positive breast cancer cells, MDA-MB-231 estrogen receptor-negative breast cancer cell line, and Ishikawa cells, using the CELLTITER-GLO (CTG)® luminescent cell viability assay. All the compounds are tested in three cell lines. Different concentration of compounds, ranging from about 0.01 nM to about 100,000 nM were delivered to $5\times10^3$ cells per well, which were then incubated for three days at 37° C., followed by CTG assay. $IC_{50}$ values were generated, as shown in Table 1. These experiments showed that the compounds of the disclosure had $IC_{50}$ values against the target breast cancer cells that were 6-10-fold less than a currently clinically available anti-breast cancer therapy, tamoxifen.

Accordingly, it is contemplated that the compounds of the present disclosure can be administered to a patient alone or as part of a composition that contains other components such as excipients, diluents, and carriers, all of which are well-known in the art. The compositions can be administered to humans and animals either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like. Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like. Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present disclosure with suitable non-irritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this disclosure include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this disclosure.

The compounds of the present disclosure can be administered to a patient at dosage levels in the range of about 0.1 to about 2,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depended on a numbers of factors including the requirements of the patient, the severity of the condition being treated, and the pharmacological activity of the compound being used. The determination of optimum dosages for a particular patient is well known to those skilled in the art.

The compounds of the present disclosure can exist in different stereoisomeric forms by virtue of the presence of asymmetric centers in the compounds. It is contemplated that all stereoisomeric forms of the compounds as well as mixtures thereof, including racemic mixtures, form part of this disclosure. In addition, the compounds of the present disclosure can exist in unsolvated as well as solvated forms with pharmaceutically acceptable solvents such as water, ethanol, and the like. In general, the solvated forms are considered equivalent to the unsolvated forms for the purposes of the present disclosure.

One aspect of the disclosure, therefore, encompasses embodiments of a compound having the structure:

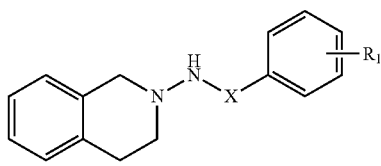

where X is carbonyl or SO$_2$; and R$_1$ can be a straight-chain alkyl group, a branched-chain alkyl group, a substituted alkyl group, an alkoxy group, or a halogen; or a salt thereof.

In embodiments of this aspect of the disclosure, R$_1$ can be CH$_3$, —OCH$_3$, or —OC$_2$H$_5$.

In embodiments of this aspect of the disclosure, the halogen can be Cl.

In embodiments of this aspect of the disclosure, the compound can be selected from the group consisting of:

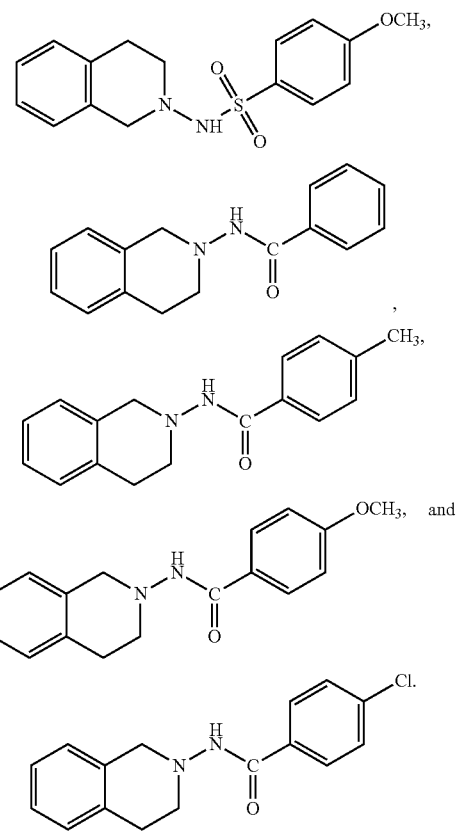

Another aspect of the disclosure encompasses embodiments of a pharmaceutically acceptable composition comprising a compound having the structure:

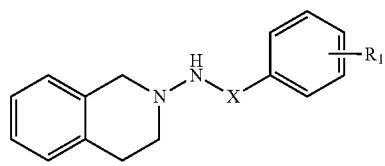

where X is carbonyl or SO$_2$; and R$_1$ can be a straight-chain alkyl group, a branched-chain alkyl group, a substituted alkyl group, an alkoxy group, or a halogen;

or a salt thereof, and a pharmaceutically acceptable carrier.

In embodiments of this aspect of the disclosure, R$_1$ can be CH$_3$, —OCH$_3$, or —OC$_2$H$_5$.

In embodiments of this aspect of the disclosure, the halogen can be Cl.

In embodiments of this aspect of the disclosure, the compound can be selected from the group consisting of:

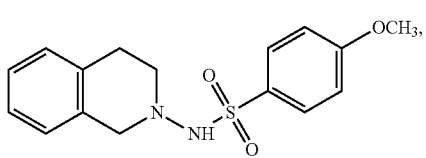

-continued

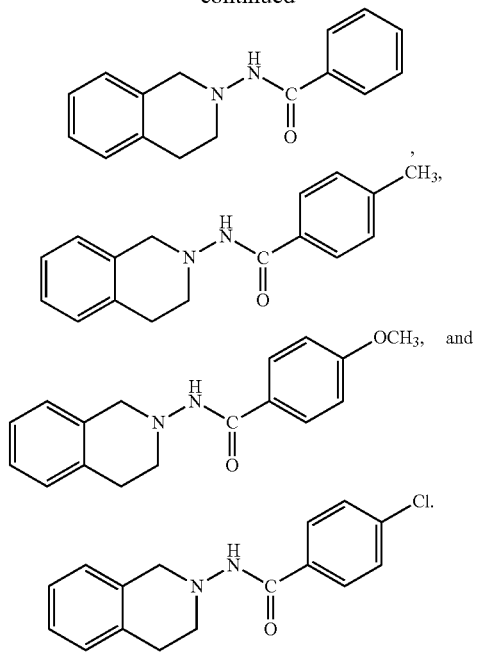

In embodiments of this aspect of the disclosure, the pharmaceutically acceptable composition can be formulated to provide an amount of the compound effective in inhibiting the proliferation of a cell cultured in vitro.

In embodiments of this aspect of the disclosure, the cell can be a cancer cell.

In some embodiments of this aspect of the disclosure, the cell can be a breast cancer cell.

In embodiments of this aspect of the disclosure, the pharmaceutically acceptable composition can be formulated to provide a therapeutically effective amount of the compound for inhibiting the proliferation of a cell in vivo.

In embodiments of this aspect of the disclosure, the in vivo cell can be a cancer cell.

In embodiments of this aspect of the disclosure, the cell can be a breast cancer cell.

Another aspect of the disclosure encompasses embodiments of a method of inhibiting the proliferation of a cell comprising contacting a cell with an effective amount of a compound having the structure:

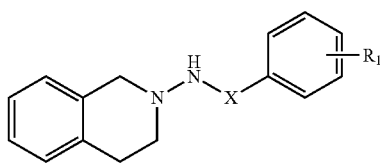

where X can be carbonyl or $SO_2$; and $R_1$ can be H, a straight-chain alkyl group, a branched-chain alkyl group, a substituted alkyl group, an alkoxy group, or a halogen; or a salt thereof, and a pharmaceutically acceptable carrier, thereby reducing the proliferation rate of the cell compared to the proliferation rate of a cell not in contact with the compound.

In some embodiments of this aspect of the disclosure, $R_1$ can be $CH_3$, $-OCH_3$, or $-OC_2H_5$.

In some embodiments of this aspect of the disclosure, the halogen can be Cl.

In embodiments of this aspect of the disclosure, the compound can be selected from the group consisting of:

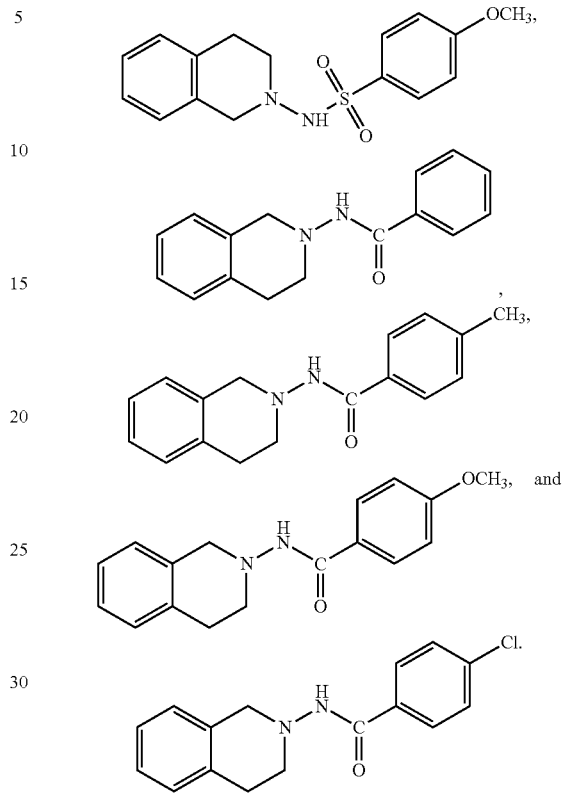

In embodiments of this aspect of the disclosure, the cell can be a cancer cell.

In embodiments of this aspect of the disclosure, the cell can be a breast cancer cell.

In embodiments of this aspect of the disclosure, the cell can be a cultured cell or a cell of an animal or human subject.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

Synthesis of 2-Aminoisoquinolinium Iodide (3)

A solution of hydroxylamine-O-sulfonic acid (2) (2 g, 1 equiv), water (10 mL) and isoquinoline (1) (6.3 mL, 3 equiv) was heated at 90° C. for 2-3 h. Potassium carbonate (2.44 g, 1 equiv) was added, and the water was evaporated. Ethanol (20-30 mL) was added to the solid residue, and insoluble potassium sulfate was filtered out. Hydroiodic acid (57%-67%, 1.34 mL, 1 equiv) was added to the filtrate, and the resulting solution was placed in a freezer. The precipitate was filtered out, washed with ethanol, and dried in vacuo. Isolated products were used as such in further reactions. Yield of the product was 1.78 g.

$^1$HNMR (CDCl$_3$) δ (ppm): 8.01 (td, J=7.2 Hz, 1H), 8.12 (td, J=7.2, 1.2 Hz, 1H), 8.30 (d, J=8.1 Hz, 1H), 8.43 (d, J=8.1 Hz, —NH$_2$, D$_2$O exchange), 8.50-8.57 (m, 4H), 9.69 (s, 1H).

Example 2

Synthesis of 2-benzimidoisoquinolinium Ylide (5a)

2-Aminoisoquinolinium iodide (2.5 g, 1 equiv) was reacted with benzoyl chloride (3.2 mL, 3 equiv) in 30 ml of 10% NaOH solution at 0° C. for 4 h and continued the reaction at room temperature for 24 h. The product was extracted with dichloromethane and dried over anhydrous sodium sulfate, filtration. The solvent was removed in vacuo and gave the crude product, which was purified by column chromatography on silica gel (200-425 mesh) using ethyl acetate:dichloromethane (2:3 v/v) as an eluent. The resultant product was obtained as a yellow color solid in 55% yield.

$^1$HNMR (CDCl$_3$) δ (ppm): 7.55-7.64 (m, 3H, C$_{3'}$, C$_{4'}$, C$_{5'}$—H), 8.20 (d, 2H, J=3.0 Hz, C$_6$, C$_7$—H), 8.31 (d, 1H, J=6.9 Hz, C$_5$—H), 8.38-8.44 (m, 4H, C$_4$, C$_8$, C$_{2'}$, C$_{6'}$—H), 8.67 (d, 1H, J=6.9 Hz, C$_3$—H), 9.93 (s, 1H, C$_1$—H).

Example 3

Synthesis of 2-(4-methylbenzimido)isoquinolinium Ylide (5b)

2-Aminoisoquinolinium iodide (3.0 g, I equiv) was reacted with 4-methylbenzoyl chloride (2.9 mL, 3 equiv) in 50 ml of 10% NaOH solution at 0° C. for 4 h and continued the reaction at room temperature for 24 h. The product was extracted with dichloromethane and dried over anhydrous sodium sulfate, filtration and solvent was removed in vacuo gave the crude product, which was purified by column chromatography on silica gel (200-425 mesh) using ethyl acetate:dichlorometh-ane (3:2 v/v) as an eluent. The resultant product was obtained as a yellow color solid in 60% yield.

$^1$HNMR (CDCl$_3$) δ (ppm): 2.38 (s, 3H, CH$_3$ group), 7.28 (d, 2H, J=8.1 Hz, C$_{3'}$, C$_{5'}$—H), 7.88-8.0 (m, 3H, C$_6$, C$_7$, C$_8$—H), 8.14 (dd, 1H, J=7.8, 7.2 Hz, C$_5$—H), 8.24 (d, 1H, J=8.4 Hz, C$_4$—H), 8.41 (dd, 2H, J=6.9, 5.4 Hz, C$_{2'}$, C$_{6'}$—H), 8.56 (dd, 1H J=2.1, 4.8 Hz, C$_3$—H), 9.89 (s, 1H, C$_1$—H).

Example 4

Synthesis of 2-(4-methoxybenzimido)isoquinolinium Ylide (5c)

2-Aminoisoquinolinium iodide (3.0 g, 1 equiv) was reacted with 4-methoxybenzoyl chloride (3.1 mL, 3 equiv) in 50 ml of 10% NaOH solution at 0.° C. for 4 h and continued the reaction at room temperature for 24 h. The product was extracted with dichloromethane and dried over anhydrous sodium sulfate, filtration and solvent was removed in vacuo gave the crude product, which was purified by column chromatography on silica gel (200-425 mesh) using ethyl acetate:dichloromethane (3:2 vh) as an eluent. The resultant product was obtained as a yellow color solid in 58% yield.

$^1$HNMR (CDCl$_3$) δ (ppm): 3.85 (s, 3H, OCH$_3$ group), 6.97 (d, 2H, J=7.2 Hz, C$_{3'}$, C$_{5'}$—H), 7.68-8.01 (m, 3H, C$_6$, C$_7$, C$_8$—H), 8.16 (dd, 1H, J=7.8, 7.2 Hz, C$_5$—H), 8.28 (d, 1H, J=8.4 Hz, C$_4$—H), 8.41 (dd, 2H, J=6.9, 5.4 Hz, C$_{2'}$, C$_{6'}$—H), 8.73 (dd, 1H, J=2.1, 4.8 Hz, C$_3$—H), 10.11 (s, 1H, C$_1$—H).

Example 5

Synthesis of 2-(4-chlorobenzimido)isoquinolinium Ylide (5d)

2-Aminoisoquinolinium iodide (2.5 g, 1 equiv) was reacted with 4-chlorobenzoyl chloride (3.5 mL, 3 equiv) in 50 ml of 10% NaOH solution at 0.° C. for 4 h and continued the reaction at room temperature for 24 h. The product was extracted with dichloromethane and dried over anhydrous sodium sulfate and filtered. Solvent was removed in vacuo to give the crude product, which was purified by column chromatography on silica gel (200-425 mesh) using ethyl acetate:dichloromethane (3:2 v/v) as an eluent. The resultant product was obtained as a yellow color solid in 70% yield.

$^1$HNMR (CDCl$_3$) δ (ppm): 7.35-7.45 (m, 2H, C$_6$, C$_7$—H), 7.75 (dd, 2H, J=1.5, 6.6 Hz, C$_{3'}$, C$_{5'}$—H), 7.83-7.89 (m, 1H, C$_5$—H), 7.97-8.17 (m, 4H, C$_4$, C$_8$, C$_{2'}$, C$_{6'}$—H), 8.24 (dd, 1H, J=1.2, 8.7 Hz, C$_3$—H), 9.38 (s, 1H, C$_1$—H).

Example 6

Synthesis of 2-(4-methoxyphenylsulfonylimido)isoquinolinium Ylide (5e)

2-Aminoisoquinolinium iodide (3.0 g, 1 equiv) was reacted with 4-methoxy benzenesulfonylchloride (4.56 g, 3 equiv) in 50 ml of 10% NaOH solution at 0.° C. for 4 h and continued the reaction at room temperature for 24 h. The product was extracted with dichloromethane and dried over anhydrous sodium sulfate and filtration. Solvent was removed in vacuo gave the crude product, which was purified by column chromatography on silica gel (200-425 mesh) using ethyl acetate:dichloromethane (3:2 v/v) as an eluent. The resultant product was obtained as a yellow color solid in 55% yield.

$^1$HNMR (CDCl$_3$) δ (ppm): 3.83 (s, 3H, OCH$_3$ group), 7.12 (d, 2H, J=7.9 Hz, C$_3$', C$_5$'—H), 7.69 (dd, 2H, J=8.1, 5.4 Hz, C$_6$, C$_7$—H), 7.99 (dd, 1H, J=1.8, 6.3 Hz, C$_5$—H), 8.10-8.14 (m, 1H, C$_8$—H), 8.15 (dd, 1H, J=7.8, 7.2 Hz, C$_2$', C$_6$'—H), 8.25 (dd, 1H, J=2.1, 8.1 Hz, C$_4$—H), 8.85 (dd, 1H, J=2.1, 6.9 Hz, C$_3$—H), 10.45 (s, 1H, C$_1$—H).

Example 7

Synthesis of N-(3,4-dihydroisoquinolin-2-(1H)-yl) benzamide (Redda-GM-3-15)

A solution of 2-benzimidoisoquinolinium Ylide (0.7 g, 1 equiv) in 20 mL absolute ethanol was added drop wise to a stirred suspension of sodium borohydride (0.43 g, 4 equiv) in 20 mL of ethanol over a period or 30 min. The resulting solution was stirred for 7 h at 0° C. The reaction mixture was treated with 10 g of ice and allowed to warm up to 25° C. The product was extracted with dichloromethane (500 ml) and dried over anhydrous sodium sulfate. The dichloromethane filtrate was evaporated in vacuo and the product chromatographed on a column of silica gel using ethyl acetate:dichloromethane (2:3 v/v) as an eluent to furnish Redda-GM-3-15 as a white solid in a 60% yield.

$^1$HNMR (CDCl$_3$) δ (ppm): 3.06 (t, 2H, J=5.7 Hz, C$_4$—H), 3.34 (t, 2H, J=6.0 Hz, C$_3$—H), 4.21 (s, 2H, C$_1$—H), 7.01 (d, 1H, J=3.0 Hz, C$_7$—H), 7.08 (s, 1H, —NH, D$_2$O exchange), 7.14-7.18 (m, 3H, C$_3$', C$_4$', C$_5$'—H), 7.39-7.50 (m, 3H, C$_5$, C$_6$, C$_8$—H), 7.75 (d, 2H, J=7.5 Hz, C$_2$', C$_6$'—H).

Example 8

Synthesis of N-(3,4-dihydroisoquinolin-2(1H)-yl-4-methylbenzamide (Redda-GM-3-19)

A solution of 2-(4-methylbenzimido)isoquinolinium Ylide (0.7 g, 1 equiv) in 20 mL absolute ethanol was added drop wise to a stirred suspension of sodium borohydride (0.43 g, 4 equiv) in 20 mL of ethanol over a period or 30 min. The resulting solution was stirred for 7 h at 0° C. The reaction mixture was treated with 10 g of ice and allowed to warm up to 25° C. The product was extracted with dichloromethane (500 mL) and dried over anhydrous sodium sulfate. The dichloromethane filtrate was evaporated in vacuo and the product chromatographed on a column of silica gel using ethyl acetate:dichloromethane (2:3 v/v) as an eluent to furnish Redda-GM-3-19 as a white solid in 65% yield.

$^1$HNMR (CDCl$_3$) δ (ppm): 2.39 (s, 3H, CH$_3$ group), 3.06 (t, 2H, J=5.7 Hz, C$_4$—H), 3.35 (t, 2H, J=6.0 Hz, C$_3$—H), 4.21 (s, 2H, C$_1$—H), 7.03 (d, 1H, J=6.9 Hz, C$_7$—H), 7.11 (s, 1H, —NH, D$_2$O exchange), 7.13-7.18 (m, 3H, C$_5$, C$_6$, C$_8$—H), 7.66 (d, 2H, J=7.8 Hz, C$_3$', C$_5$'—H), 7.76 (d, 2H, J=7.5 Hz, C$_2$', C$_6$'—H).

Example 9

Synthesis of N-(3,4-dihydroisoquinolin-2(1H)-yl)-4-methoxybenzamide (Redda-GM-3-16)

A solution of 2-(4-methoxybenzimido)isoquinolinium Ylide (0.5 g, 1 equiv) in 20 mL absolute ethanol was added drop wise to a stirred suspension of sodium borohydride (0.43 g, 4 equiv) in 10 mL of ethanol over a period or 30 min. The resulting solution was stirred for 7 h at 0° C. The reaction mixture was treated with 10 g of ice and allowed to warm up to 25° C. The product was extracted with dichloromethane (500 mL) and dried over anhydrous sodium sulfate. The dichloromethane filtrate was evaporated in vacuo and the product chromatographed on a column of silica gel using ethyl acetate:dichloromethane (2:3 v/v) as an eluent to furnish Redda-GM-3-16 as a white solid in 60% yield.

$^1$HNMR (CDCl$_3$) δ (ppm): 3.05 (t, 2H, J=5.7 Hz, C$_4$—H), 3.33 (t, 2H, J=6.0 Hz, C$_3$—H), 3.84 (s, 3H, OCH$_3$ group), 4.19 (s, 2H, C$_1$—H), 6.90 (d, 2H, J=9.0 Hz, C$_3$', C$_5$'—H), 7.01 (d, 1H, J=3.0 Hz, C$_5$—H), 7.13 (s, 1H, —NH, D$_2$O exchange), 7.14-7.18 (m, 3H, C$_6$, C$_7$, C$_8$—H), 7.72 (d, 2H, J=8.1 Hz, C$_2$', C$_6$'—H).

Example 10

Synthesis of 4-chloro-N-(3,4-dihydroisoquinolin-2 (1H)-yl)bemamide (Redda-GM-3-18)

A solution of 2-(4chlorobenzimido)isoquinolinium Ylide (0.7 g, 1 equiv) in 20 mL absolute ethanol was added drop wise to a stirred suspension of sodium borohydride (0.43 g, 4 equiv) in 20 mL of ethanol over a period or 30 min. The resulting solution was stirred for 7 h at 0° C. The reaction mixture was treated with 10 g of ice and allowed to warm up to 25° C. The product was extracted with dichloromethane (500 mL) and dried over anhydrous sodium sulfate. The dichloromethane filtrate was evaporated in vacuo and the product chromatographed on a column of silica gel using ethyl acetate:dichloromethane (2:3 v/v) as an eluent to furnish Redda-GM-3-18 as a white solid in 70% yield.

$^1$HNMR (CDCl$_3$) δ (ppm): 3.07 (t, 2H, J=5.7 Hz, C$_4$—H), 3.32 (t, 2H, J=6.0 Hz, C$_3$—H), 4.19 (s, 2H, C$_1$—H), 7.02 (d, 1H, J=2.4 Hz, C$_7$—H), 7.04 (s, 1H, —NH, D$_2$O exchange), 7.14-7.19 (m, 3H, C$_5$, C$_6$, C$_8$—H), 7.26 (d, 2H, J=8.2 Hz, C$_3$', C$_5$'—H), 7.69 (d, 2H, J=8.1 Hz, C$_2$', C$_6$'—H).

Example 11

Synthesis of N-(3,4-dihydroisoquinolin-2(1H)-yl)-4-methoxybenzenesulfonamide (Redda-GM-3-13)

A solution of 2-(4-methoxyphenylsulfonylimido)isoquinolinium Ylide (0.7 g, 1 equiv) in 20 mL absolute ethanol was added drop wise to a stirred suspension of sodium borohydride (0.43 g, 4 equiv) in 20 mL of ethanol over a period or 30 min. The resulting solution was stirred for 7 h at 0° C. The reaction mixture was treated with 10 g of ice and allowed to warm to 25° C. The product was extracted with dichloromethane (500 mL) and dried over anhydrous sodium sulfate. The dichloromethane filtrate was evaporated in vacuo and the product chromatographed on a column of silica gel using ethyl acetate:dichloromethane (2:3 v/v) as an eluent to furnish Redda-GM-S13 as a white solid in 58% yield.

$^1$HNMR (CDCl$_3$) δ (ppm): 3.06 (t, 2H, J=5.1 Hz, C$_4$—H), 3.34 (t, 2H, J=7.5 Hz, C$_3$—H), 3.84 (s, 3H, OCH$_3$ group), 4.21 (s, 2H, C$_1$—H), 6.91 (d, 2H, J=9.0 Hz, C$_3$', C$_5$'—H), 7.01 (d, 1H, J 2.1 Hz, C$_7$—H), 7.04 (s, 1H, —NH, D$_2$O exchange), 7.11-7.18 (m, 3H, C$_5$, C$_6$, C$_8$—H), 7.72 (d, 2H, J=7.8 Hz, C$_2$', C$_6$'—H).

Example 12

Compounds Redda-GM-3-13, Redda-GM-3-15, Redda-GM-3-16, Redda-GM-3-18, and Redda-GM-3-19 were tested for their cytotoxic effects on MCF-7 estrogen receptor-positive breast cancer cells, MDA-MB-231 estrogen receptor-negative breast cancer cell line, and Ishikawa cells, using the CELLTITER-GLO® luminescent cell viability assay (Promega, Madison, Wis.) following the manufacturer's instruction.

CELLTITER-GLO® is a homogeneous method based on the quantification of ATP, which is an indicator of metabolically active cells. In this assay, the number of viable cells in culture is determined based on the quantification of ATP present, which signals the presence of metabolically active cells. Damaged cells are not detected as the ATP leaked from these cells is quickly consumed by ATPases that are also released upon damage). The amount of ATP is determined using a system based on luciferase and D-luciferin resulting in light generation.

The cell lines were plated in 13, 96 well plates at a density of 5000 cells/well in total volumes of 50 μL in phenol-red free medium and incubated for overnight. Compounds Redda-GM-3-13, Redda-GM-3-15, Redda-GM-3-16, Redda-GM-3-18, and Redda-GM-3-19 were weighed and dissolved in DMSO (10 mM) and tested at different concentrations ranging from 0.01 to 100,000 nM, using Tamoxifen (10 μM) as a positive control.

25 μL of 40 nM estradiol should be added to all appropriate wells on the plate. 25 μL media were added to all wells that did not receive estradiol. 25 μL of stocks (containing the compounds to be tested, DMSO and phenol-red free medium) were added to cells and medium already on plate. 50 μL of medium were added to media wells, and 50 μL of mix (contain 32 mL DMSO+768 mL phenol-red free medium) to all vehicle control wells. Tamoxifen (10 μM) was also added to appropriate wells.

Drug-exposed cells were incubated or 72 h at 37° C. in a 5% $CO_2$ incubator, after which the plates were removed for CELLTITER-GLO® assay and equilibrated at room temperature for 30 min. 100 μL of CELLTITER-GLO® assay reagent was added to each well and cell-lysis was induced on an orbital shaker for 2 min. followed by a further 10 min incubation at room temperature. Luminescence results were read on TriLux Luminometer. The luminescent signal is proportional to the number of active cells present in culture. Dead cells did not affect cell counts because they did not contribute to ATP content. As a consequence, the number of metabolically active cells can be directly derived from the luminescent signal using a specific calibration curve. Data were expressed as percentage of untreated control (i.e. treatment value-blank/vehicle value blank), mean±SE for three replications. The $IC_{50}$ values, as shown in Table 1, were determined using GraphPad Prism 4 dose-response curve fitting.

TABLE I

In vitro Anticancer Activity of Substituted Tetrahydroisoquinolines against Breast Cancer cell lines

| | STRUCTURE | $IC_{50}$ μg/mL | | |
| --- | --- | --- | --- | --- |
| | | MCF-7 | ISHIKAWA | MDA-MB-231 |
| Redda-CM-3-13 | 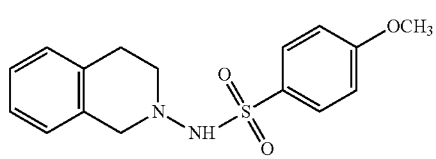 [SMILES: COc1ccc(S(=O)(=O)NN2CCc3ccccc3C2)cc1] | 1.27 | 0.45 | 0.76 |
| Redda-GM-3-15 | 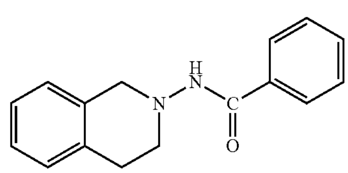 [SMILES: O=C(NN1CCc2ccccc2C1)c1ccccc1] | 0.63 | 0.23 | 0.74 |
| Redda-GM-3-16 | 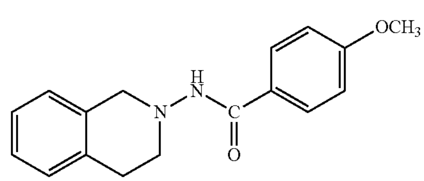 [SMILES: COc1ccc(C(=O)NN2CCc3ccccc3C2)cc1] | 0.93 | 0.21 | 0.78 |
| Redda-GM-3-18 | 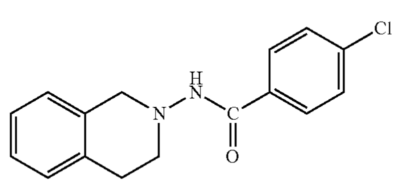 [SMILES: O=C(NN1CCc2ccccc2C1)c1ccc(Cl)cc1] | 0.71 | 0.61 | 0.80 |

TABLE I-continued

In vitro Anticancer Activity of Substituted Tetrahydroisoquinolines against Breast Cancer cell lines

| | STRUCTURE | IC$_{50}$ μg/mL | | |
|---|---|---|---|---|
| | | MCF-7 | ISHIKAWA | MDA-MB-231 |
| Redda-GM-3-19 | 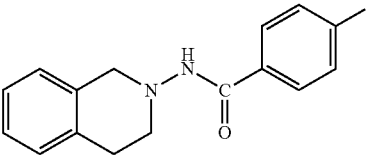 | 0.70 | 0.44 | 1.02 |
| Tamoxifen | | 6.21 | 6.11 | 5.98 |

We claim:

1. A compound having the structure:

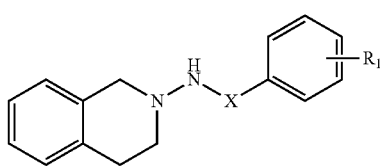

wherein, when X is carbonyl, R$_1$ is a straight-chain alkyl group, a branched-chain alkyl group, a substituted alkyl group, an alkoxy group, or a halogen, and when X is SO$_2$ R$_1$ is H, a branched-chain alkyl group, a substituted alkyl group, an alkoxy group, or a halogen;

or a salt thereof.

2. The compound of claim 1, wherein, when X is carbonyl, R$_1$ is CH$_3$, —OCH$_3$, or —OC$_2$H$_5$, and when X is SO$_2$, R$_1$ is —OCH$_3$, or —OC$_2$H$_5$.

3. The compound of claim 1, wherein R$_1$ is Cl.

4. The compound of claim 1, wherein the compound is selected from the group consisting of

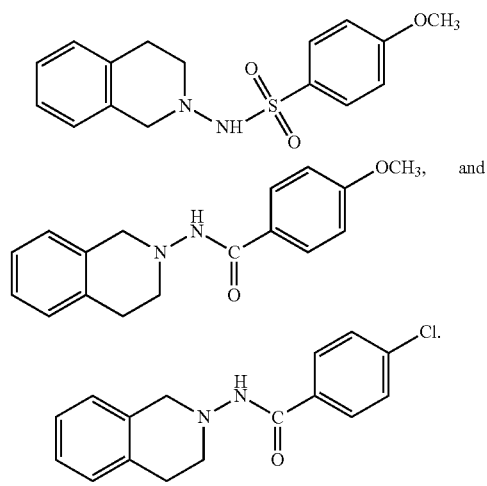

5. A pharmaceutically acceptable composition comprising a compound having the structure:

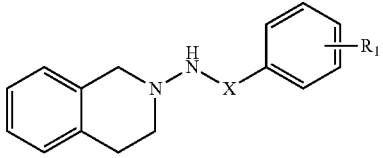

wherein:

X is carbonyl or SO$_2$; and

R$_1$ is H, a straight-chain alkyl group, a branched-chain alkyl group, a substituted alkyl group, an alkoxy group, or a halogen;

or a salt thereof, and a pharmaceutically acceptable carrier.

6. The pharmaceutically acceptable composition of claim 5, wherein R$_1$ is CH$_3$, —OCH$_3$, or —OC$_2$H$_5$.

7. The pharmaceutically acceptable composition of claim 5, wherein the halogen is Cl.

8. The pharmaceutically acceptable composition of claim 5, wherein the compound is selected from the group consisting of:

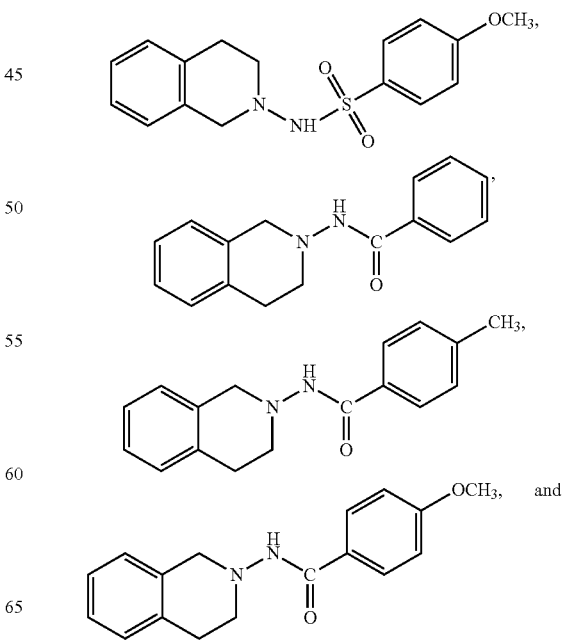

-continued

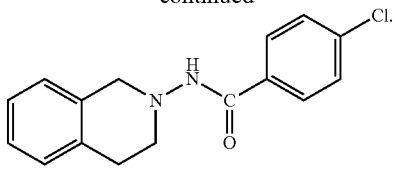

9. The pharmaceutically acceptable composition according to claim 5, wherein said pharmaceutically acceptable composition is formulated to provide an amount of the compound effective in inhibiting the proliferation of a cell cultured in vitro.

10. The pharmaceutically acceptable composition according to claim 9, wherein the cell is a cancer cell.

11. The pharmaceutically acceptable composition according to claim 9, wherein the cell is a breast cancer cell.

12. The pharmaceutically acceptable composition according to claim 5, wherein said pharmaceutically acceptable composition is formulated to provide a therapeutically effective amount of the compound for inhibiting the proliferation of a cell in vivo.

13. The pharmaceutically acceptable composition according to claim 12, wherein the cell is a cancer cell.

14. The pharmaceutically acceptable composition according to claim 12, wherein the cell is a breast cancer cell.

15. A method of inhibiting the proliferation of a breast cancer cell comprising contacting a breast cancer cell with an effective amount of a compound having the structure:

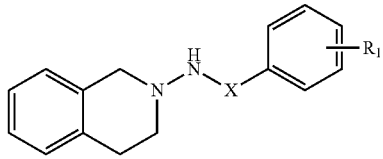

wherein, when X is carbonyl, $R_1$ is a straight-chain alkyl group, a branched-chain alkyl group, a substituted alkyl group, an alkoxy group, or a halogen, and when X is $SO_2$, $R_1$ is H, a branched-chain alkyl group, a substituted alkyl group, an alkoxy group, or a halogen;
or a salt thereof.

16. The method of claim 15, wherein, when X is carbonyl, $R_1$ is $CH_3$, —$OCH_3$, or —$OC_2H_5$, and when X is $SO_2$, $R_1$ is —$OCH_3$ or —$OC_2H_5$.

17. The method of claim 16, wherein the halogen is Cl.

18. The method of claim 15, wherein the compound is selected from the group consisting of:

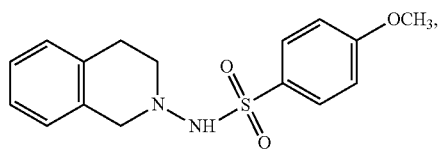

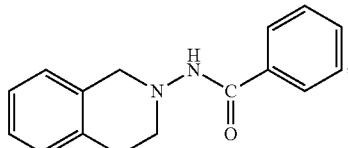

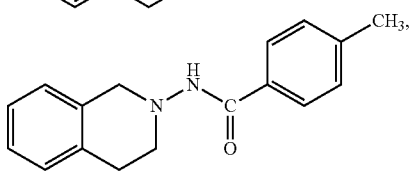

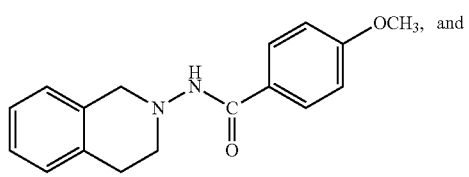

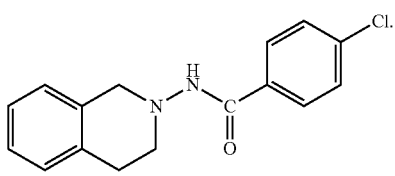

19. The method of claim 15, wherein the cell is a cultured cell or a cell of an animal or human subject.

* * * * *